(12) United States Patent
Seex

(10) Patent No.: US 11,801,061 B2
(45) Date of Patent: Oct. 31, 2023

(54) SYSTEM AND METHOD FOR INSERTING AN INTERVERTEBRAL CAGE INTO A SPINE

(71) Applicant: Retrospine Pty Ltd, Sydney (AU)

(72) Inventor: Kevin Seex, Sydney (AU)

(73) Assignee: RETROSPINE PTY LTD, Sydney (AU)

( * ) Notice: Subject to any disclaimer, the term of this patent is extended or adjusted under 35 U.S.C. 154(b) by 44 days.

(21) Appl. No.: 16/285,027

(22) Filed: Feb. 25, 2019

(65) Prior Publication Data

US 2019/0321055 A1  Oct. 24, 2019

Related U.S. Application Data

(63) Continuation of application No. 16/151,214, filed on Oct. 3, 2018, now abandoned, which is a continuation
(Continued)

(30) Foreign Application Priority Data

Dec. 8, 2012  (AU) ................................ 2012905345

(51) Int. Cl.
*A61F 2/46*  (2006.01)
*A61B 17/16*  (2006.01)
(Continued)

(52) U.S. Cl.
CPC ...... *A61B 17/1659* (2013.01); *A61B 17/1671* (2013.01); *A61B 17/7074* (2013.01);
(Continued)

(58) Field of Classification Search
CPC ............ A61F 2/4611; A61F 2002/4627; A61F 2002/4628; A61F 2002/4629
See application file for complete search history.

(56) References Cited

U.S. PATENT DOCUMENTS

| 4,716,894 A | * | 1/1988 | Lazzeri | ................. A61F 2/4609 606/91 |
| 5,531,749 A | | 7/1996 | Michelson | |
| | | | (Continued) | |

FOREIGN PATENT DOCUMENTS

| CN | 104771251 | 7/2015 |
| EP | 1391189 | 4/2008 |
| | (Continued) | |

OTHER PUBLICATIONS

PCT International Search Report, PCT/AU2013/001425 dated Feb. 10, 2014. pp. 1-4.
(Continued)

*Primary Examiner* — Anu Ramana
(74) *Attorney, Agent, or Firm* — MORRISS O'BRYANT COMPAGNI CANNON, PLLC

(57) ABSTRACT

The present disclosure includes a surgical insertion tool that may have a handle having a longitudinal axis, an extended arm that may be fixed to the handle and have at least two bends to avoid bony features during insertion of an instrument, and an attachment feature configured to attach the instrument to the insertion tool such that the longitudinal axis of the handle intersects the instrument.

10 Claims, 12 Drawing Sheets

Related U.S. Application Data of application No. 15/947,676, filed on Apr. 6, 2018, now abandoned, which is a continuation of application No. 15/725,168, filed on Oct. 4, 2017, now abandoned, which is a continuation of application No. 15/216,635, filed on Jul. 21, 2016, now abandoned, which is a continuation of application No. 15/061,958, filed on Mar. 4, 2016, now abandoned, said application No. 16/151,214 is a continuation of application No. 14/650,424, filed as application No. PCT/AU2013/001425 on Dec. 8, 2013, now abandoned, said application No. 15/061,958 is a continuation of application No. 14/574,342, filed on Dec. 17, 2014, now abandoned.

(60) Provisional application No. 61/917,265, filed on Dec. 17, 2013.

(51) Int. Cl.
  *A61B 17/70* (2006.01)
  *A61F 2/44* (2006.01)
  *A61B 17/00* (2006.01)
  *A61B 90/00* (2016.01)

(52) U.S. Cl.
  CPC .............. *A61F 2/44* (2013.01); *A61F 2/4684* (2013.01); *A61B 2017/00464* (2013.01); *A61B 2090/062* (2016.02); *A61F 2/4611* (2013.01)

(56) References Cited

U.S. PATENT DOCUMENTS

| | | | |
|---|---|---|---|
| 5,569,298 A | 10/1996 | Schnell | |
| 6,423,073 B2 | 7/2002 | Bowman | |
| 6,425,920 B1 | 7/2002 | Hamada | |
| 7,135,043 B2 | 11/2006 | Nakahara et al. | |
| 7,232,463 B2 | 6/2007 | Falahee | |
| 7,591,852 B2* | 9/2009 | Prosser | A61F 2/4611 623/17.11 |
| 7,708,743 B2* | 5/2010 | Anderson | A61B 17/8872 606/99 |
| 7,749,251 B2* | 7/2010 | Obenchain | A61B 17/8605 606/247 |
| 7,862,593 B2 | 1/2011 | Clement et al. | |
| 7,905,886 B1* | 3/2011 | Curran | A61F 2/4611 606/99 |
| 7,959,675 B2* | 6/2011 | Gately | A61F 2/4611 623/17.11 |
| 7,988,695 B2* | 8/2011 | Dye | A61F 2/4611 606/86 A |
| 8,016,829 B2 | 9/2011 | Mahoney et al. | |
| 8,083,778 B2 | 12/2011 | Clement et al. | |
| 8,088,163 B1 | 1/2012 | Kleiner | |
| 8,097,027 B2* | 1/2012 | Lim | A61B 17/808 606/279 |
| 8,114,139 B2 | 2/2012 | Sournac et al. | |
| D656,610 S | 3/2012 | Kleiner | |
| 8,277,510 B2 | 10/2012 | Kleiner | |
| 8,292,960 B2 | 10/2012 | Kleiner | |
| 8,366,748 B2 | 2/2013 | Kleiner | |
| 8,419,795 B2 | 4/2013 | Sweeney | |
| 8,506,632 B2 | 8/2013 | Ganem et al. | |
| 8,506,636 B2 | 8/2013 | Dye | |
| 8,715,355 B2 | 5/2014 | Kleiner | |
| 8,801,786 B2 | 8/2014 | Bernard et al. | |
| 8,808,305 B2 | 8/2014 | Kleiner | |
| 8,840,620 B2 | 9/2014 | Recoules-Arche et al. | |
| 8,840,666 B2 | 9/2014 | Crozet | |
| 8,845,733 B2 | 9/2014 | O'Neil et al. | |
| 8,852,278 B2 | 10/2014 | Bellas | |
| 8,864,764 B2 | 10/2014 | Groiso | |
| 8,986,307 B2* | 3/2015 | Kirschman | A61F 2/4465 606/86 A |
| 9,078,706 B2 | 7/2015 | Kirschman | |
| 9,101,492 B2 | 8/2015 | Mangione et al. | |
| 9,119,729 B2 | 9/2015 | Falahee | |
| 9,180,024 B2 | 11/2015 | Mahoney et al. | |
| 9,186,193 B2 | 11/2015 | Kleiner et al. | |
| 9,216,096 B2 | 12/2015 | Lynn et al. | |
| 2002/0147460 A1 | 10/2002 | Bacher | |
| 2002/0165550 A1 | 11/2002 | Frey et al. | |
| 2003/0139812 A1 | 7/2003 | Garcia et al. | |
| 2006/0235426 A1* | 10/2006 | Lim | A61F 2/4611 606/99 |
| 2006/0276816 A1 | 12/2006 | Eckman | |
| 2007/0100339 A1 | 5/2007 | Clement et al. | |
| 2007/0276406 A1 | 11/2007 | Mahoney et al. | |
| 2007/0293949 A1 | 12/2007 | Salemi et al. | |
| 2008/0097454 A1 | 4/2008 | DeRidder et al. | |
| 2008/0306489 A1* | 12/2008 | Altarac | A61F 2/4611 606/99 |
| 2008/0306557 A1* | 12/2008 | Altarac | A61F 2/4611 606/86 A |
| 2009/0082811 A1 | 3/2009 | Stad et al. | |
| 2009/0209998 A1 | 8/2009 | Widmann | |
| 2009/0234364 A1* | 9/2009 | Crook | A61F 2/4465 606/99 |
| 2010/0082030 A1 | 4/2010 | Groiso | |
| 2010/0087822 A1 | 4/2010 | Groiso | |
| 2011/0004222 A1 | 1/2011 | Biedermann et al. | |
| 2011/0015679 A1 | 1/2011 | Fiere et al. | |
| 2011/0087074 A1 | 4/2011 | Hardenbrook | |
| 2011/0112580 A1 | 5/2011 | Clement et al. | |
| 2011/0112581 A1 | 5/2011 | Clement | |
| 2011/0118842 A1 | 5/2011 | Bernard et al. | |
| 2011/0172769 A1 | 7/2011 | Ganem et al. | |
| 2011/0202096 A1 | 8/2011 | White et al. | |
| 2011/0276139 A1 | 11/2011 | Mahoney et al. | |
| 2012/0004684 A1 | 1/2012 | Reinauer | |
| 2012/0116512 A1 | 5/2012 | Sournac et al. | |
| 2012/0130387 A1* | 5/2012 | Simpson | A61F 2/4611 606/104 |
| 2012/0201322 A1 | 8/2012 | Rakib et al. | |
| 2012/0226358 A1 | 9/2012 | Kleiner | |
| 2012/0277867 A1 | 11/2012 | Kana et al. | |
| 2013/0053967 A1 | 2/2013 | Sournac et al. | |
| 2013/0096684 A1 | 4/2013 | Kleiner | |
| 2013/0150898 A1 | 6/2013 | Wong et al. | |
| 2013/0184825 A1 | 7/2013 | Kleiner | |
| 2013/0211524 A1 | 8/2013 | Hugues | |
| 2014/0172105 A1 | 6/2014 | Frasier et al. | |
| 2015/0025640 A1 | 1/2015 | Malandain | |
| 2015/0297247 A1 | 10/2015 | Seex | |
| 2016/0022434 A1 | 1/2016 | Robinson | |
| 2016/0030029 A1 | 2/2016 | Mahoney et al. | |
| 2016/0030190 A1 | 2/2016 | Robinson | |

FOREIGN PATENT DOCUMENTS

| | | |
|---|---|---|
| FR | 2816201 | 5/2002 |
| JP | 2007521886 | 8/2007 |
| TW | 201036587 | 10/2010 |
| TW | 201125533 | 8/2011 |
| WO | WO9529641 | 11/1995 |
| WO | WO0238086 | 5/2002 |
| WO | WO2005077288 | 8/2005 |
| WO | WO2006042335 | 4/2006 |
| WO | WO2010010522 | 1/2010 |
| WO | WO2011013047 | 2/2011 |
| WO | WO2014085870 | 6/2014 |

OTHER PUBLICATIONS

PCT Written Opinion of the International Searching Authority, PCT/AU2013/001425, dated Feb. 10, 2014. pp. 1-5.

* cited by examiner

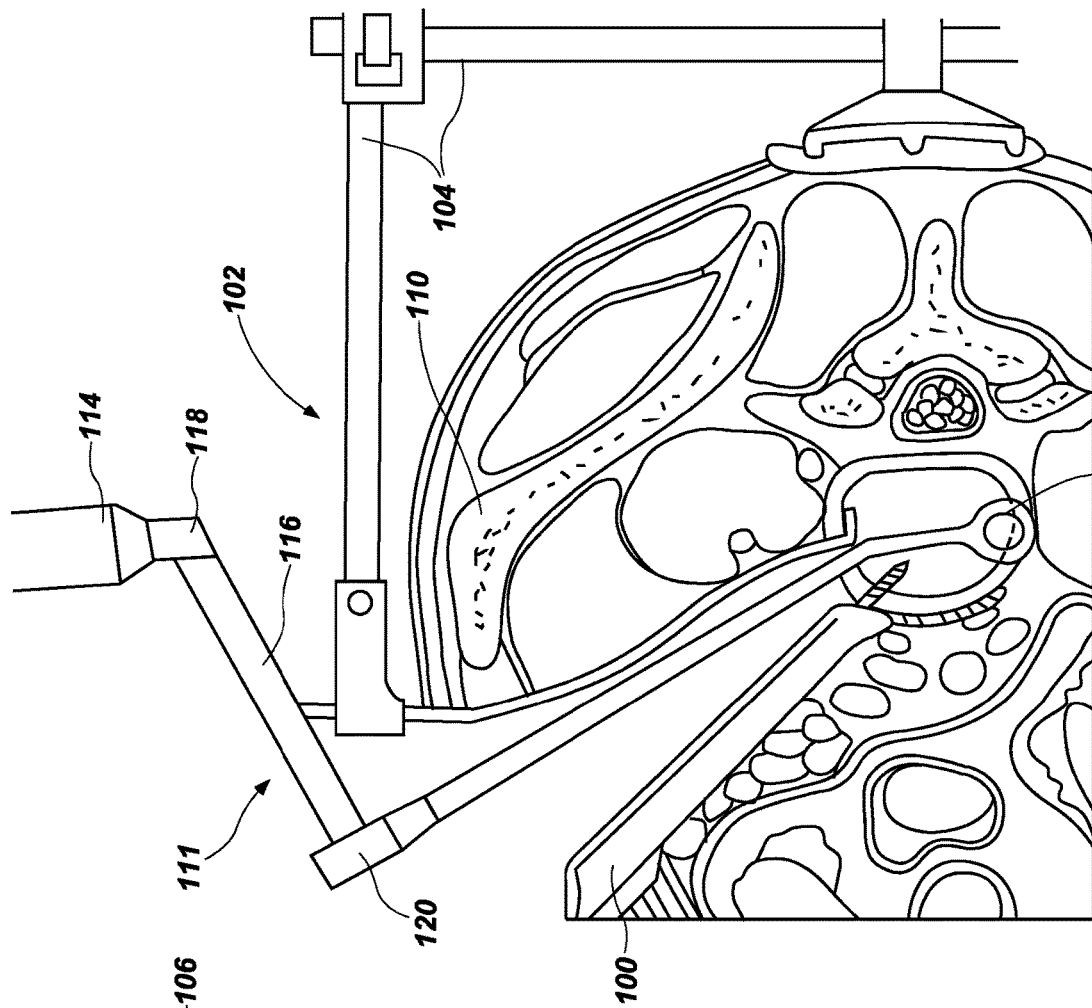
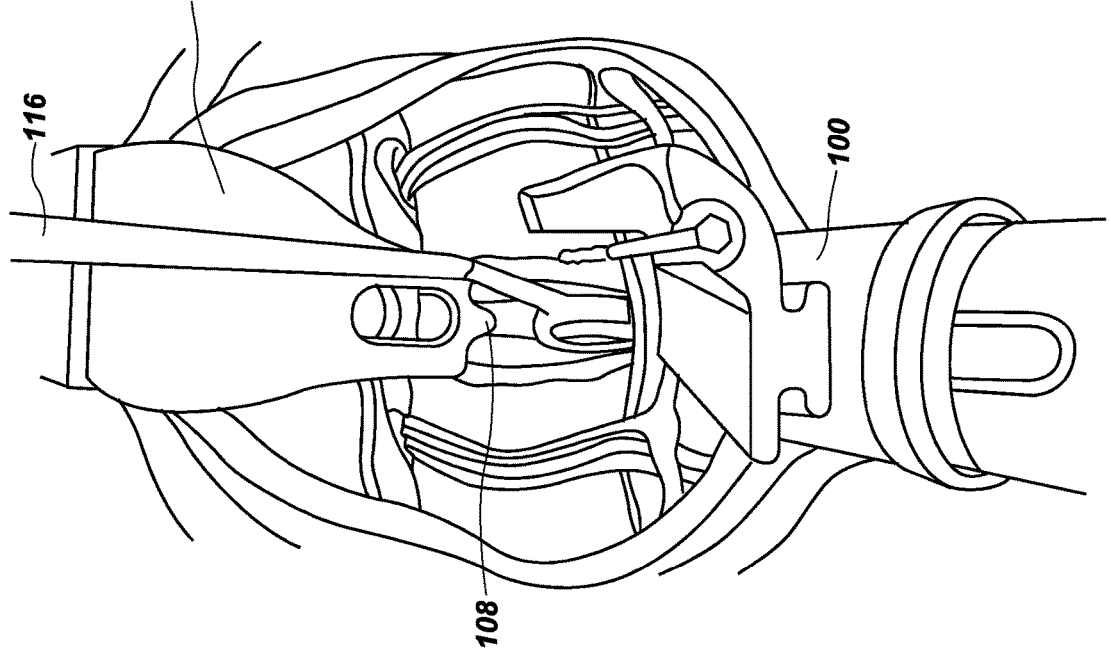
FIG. 3B
FIG. 3A

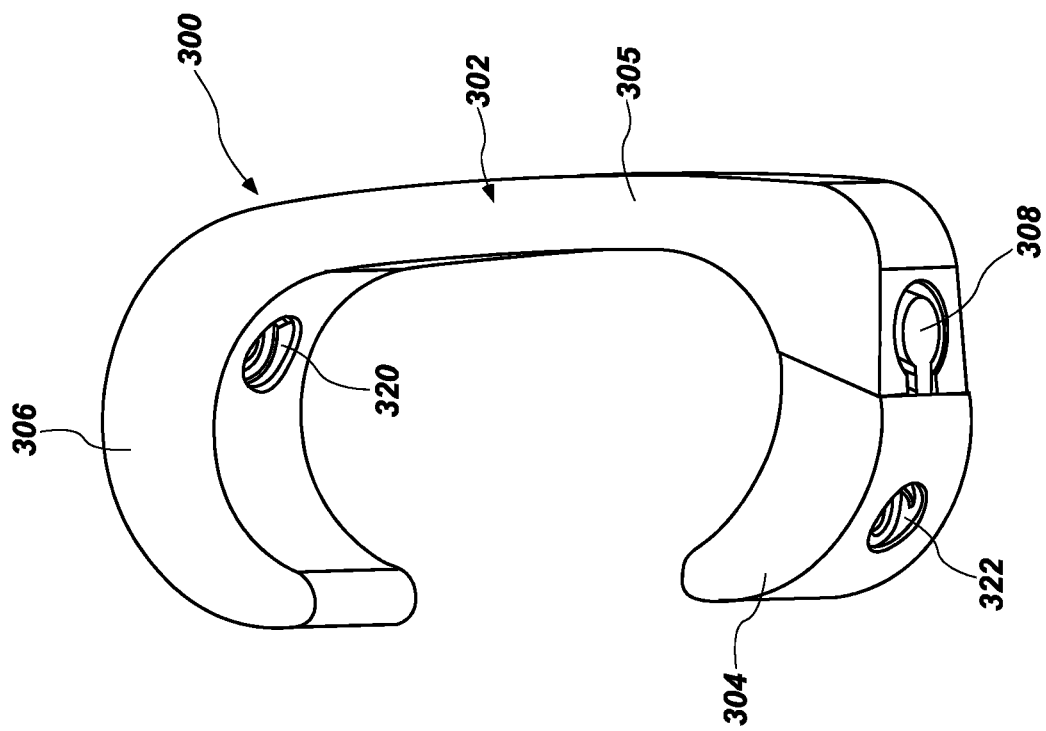
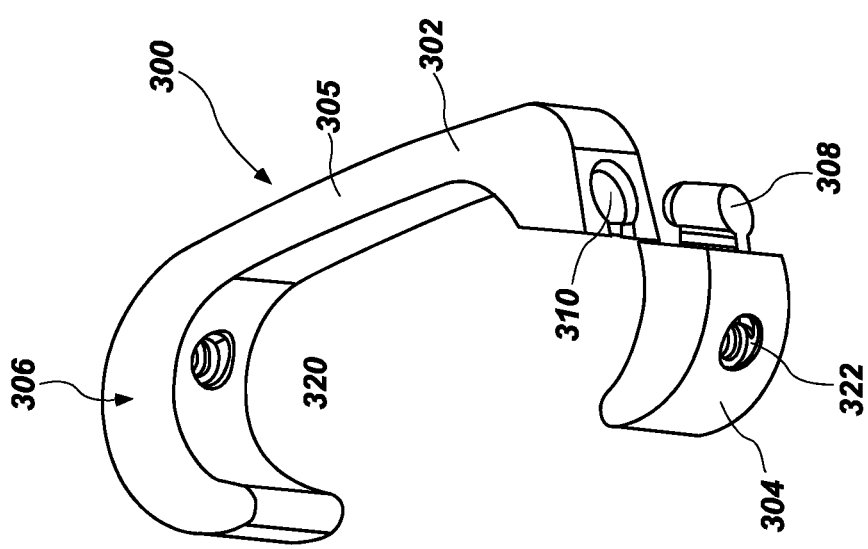

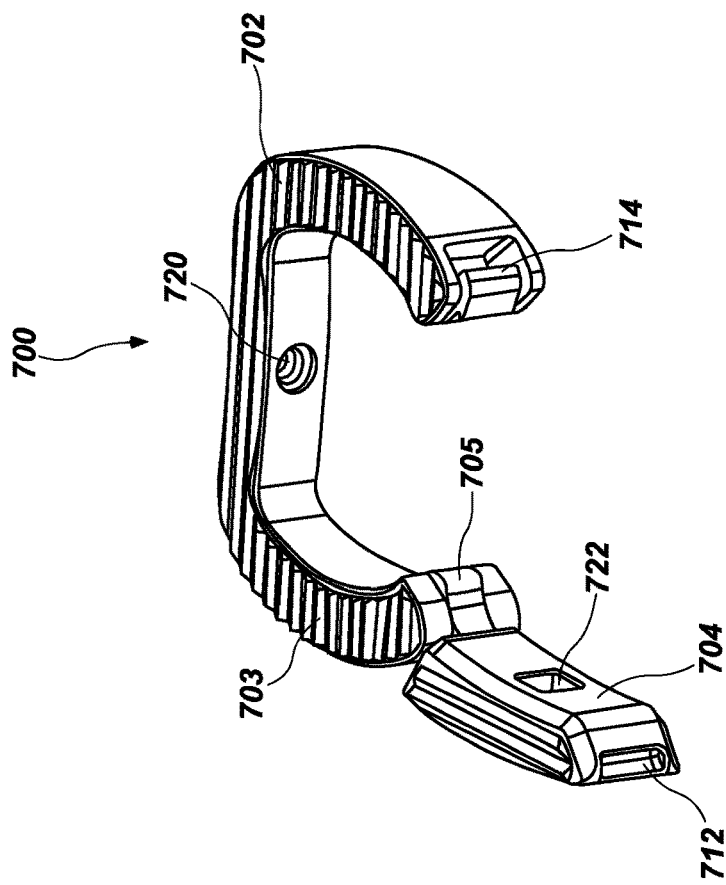
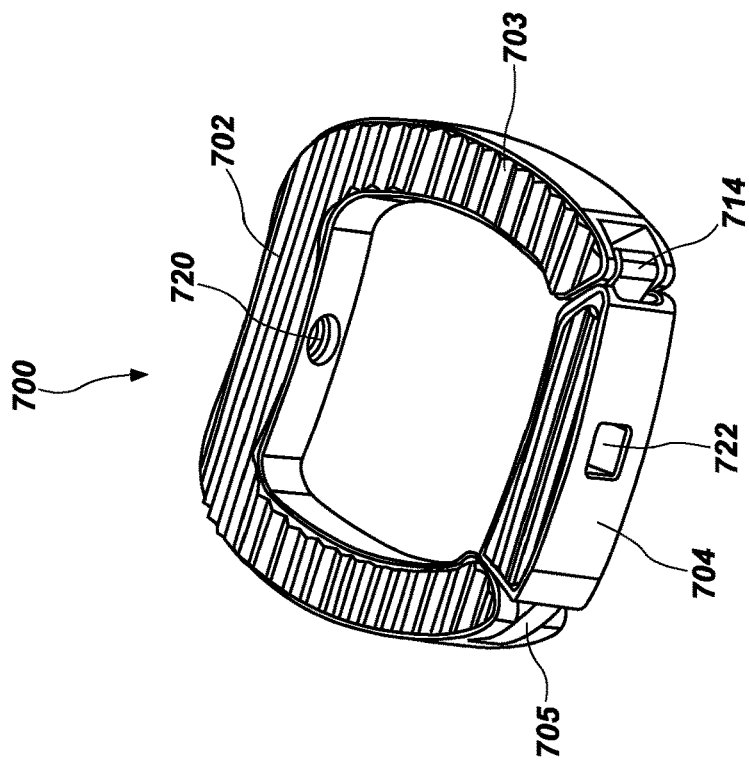

SYSTEM AND METHOD FOR INSERTING AN INTERVERTEBRAL CAGE INTO A SPINE

CROSS-REFERENCE TO RELATED APPLICATIONS

This application is a continuation of U.S. patent application Ser. No. 16/151,214, filed Oct. 3, 2018, which is a continuation of U.S. patent application Ser. No. 15/947,676, filed Apr. 6, 2018, which is a continuation of U.S. patent application Ser. No. 15/725,168, filed Oct. 4, 2017, which is a continuation of U.S. patent application Ser. No. 15/216,635, filed Jul. 21, 2016, which is a continuation of U.S. patent application Ser. No. 15/061,958, filed Mar. 4, 2016, which is a continuation of prior U.S. patent application Ser. No. 14/574,342, filed Dec. 17, 2014, which claims the benefit of U.S. Provisional Application No. 61/917,265, filed Dec. 17, 2013, and U.S. patent application Ser. No. 16/151,214, filed Oct. 3, 2018, is also a continuation of U.S. patent application Ser. No. 14/650,424, filed Jun. 8, 2015 which is a National Stage Entry of PCT Application No. PCT/AU2013/001425, filed on Dec. 8, 2013, which claims the benefit of Australian Provisional Application No. 2012905345, filed Dec. 8, 2012, which are hereby incorporated by reference herein in their entireties, including but not limited to those portions that specifically appear hereinafter, the incorporation by reference being made with the following exception: In the event that any portion of the above-referenced applications are inconsistent with this application, this application supercedes said above-referenced applications.

STATEMENT REGARDING FEDERALLY SPONSORED RESEARCH OR DEVELOPMENT

Not Applicable.

BACKGROUND

1. The Field of the Present Disclosure

The present disclosure relates generally to intervertebral cages and insertion devices and methods, and in particular to an Anterior To Psoas (ATP) approach to the lumbar spine. The term "ATP" as used herein shall refer to an Anterior To Psoas approach to the lumbar spine.

2. Description of Related Art

Spinal fusion is surgery to permanently connect two or more vertebrae in a spine, eliminating motion between them. Spinal fusion may improve stability, correct a deformity or reduce pain. Spinal fusion may involve placing extra bone (bone graft) to fill the space between two spinal vertebrae. The bone graft material used in spinal fusion may be in a preformed shape, or it may be contained within a plastic, carbon fiber or metal cage. A surgeon may use plates, screws or rods to hold the vertebrae and graft in place to promote healing after spinal fusion. Once the bone graft heals, the vertebrae are permanently connected.

Intervertebral cages are well known in the art for use in placing and anchoring bone grafts during spinal fusion. Intervertebral cages are packed with bone graft material and are inserted into the spine after a discectomy to provide structural support to the endplate of the vertebra, by maintaining height and improve stability of the endplate. The intervertebral cages expose the bone graft material to the exposed endplate to enhance bony fusion of the immediately adjacent vertebra.

As shown in FIG. 1, intervertebral cages have been conventionally used in a variety of different forms, for example, posterior lumbar interbody fusion (PLIF) 1, lateral lumbar interbody fusion (LLIF) 2, transforminal lumbar interbody fusion (TLIF) 3, and anterior lumbar interbody fusion (ALIF) 4. Additionally, intervertebral cages can be solid, hollow, expandable, and include varying shapes and sizes, such as rectangular, round or anatomical.

The lumbar spine may be fused from various approaches including, anterior, lateral, posterior or anterolateral. Interbody fusion is an essential part of spinal fusion from each of these fusion approaches. To facilitate interbody fusion, the degenerate disc is removed from the intervertebral space and replaced with at least one intervertebral cage. The cage and the vacated intervertebral space are filled with bone graft or graft like material. Fusion then occurs with bone growing from the endplates through the graft.

Conventional disc preparation during an interbody fusion procedure include, clearing the vacated disc space of disc material with rongeurs. Bony endplates of adjacent discs are prepared by removing all attached cartilage by scraping these surfaces with curettes and rakes, ideally creating a receptive surface, "bleeding zone", for the graft to contact the endplate. The intervertebral cage is then packed with grafting material and inserted into the prepared disc space via impaction. Interbody fusion occurs when a patients own bone grows across from one endplate of a vertebra, through the graft material, and reaches the other endplate of the immediately adjacent vertebra.

The conventional approaches to interbody fusion, specifically anterior or lateral approaches, are characterized by several disadvantages that are addressed by the present disclosure. For example, the present disclosure minimizes, and in some aspects eliminates, endplate injury during endplate preparation, cage subsidence, poor cage positioning as a result of cage subsidence, inadequate endplate preparation, bone graft material falling out of cage during impaction, inadequate contact between endplates and the bone graft material within the intervertebral cage and other problems, by utilizing the methods and structural features described herein.

The features and advantages of the present disclosure will be set forth in the description which follows, and in part will be apparent from the description, or may be learned by the practice of the present disclosure without undue experimentation. The features and advantages of the present disclosure may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which:

FIG. 3A is a top view of another embodiment of the present disclosure;

FIG. 3B is a cross-sectional side view of another embodiment of the present disclosure;

FIG. 7A is an exploded perspective view of an intervertebral cage of the present disclosure;

FIG. 7B is a perspective view of an intervertebral cage of the present disclosure;

FIG. 11A are perspective views of another intervertebral cage of the present disclosure;

FIG. 11B are perspective views of an open intervertebral cage of the present disclosure.

DETAILED DESCRIPTION

Figure 1:
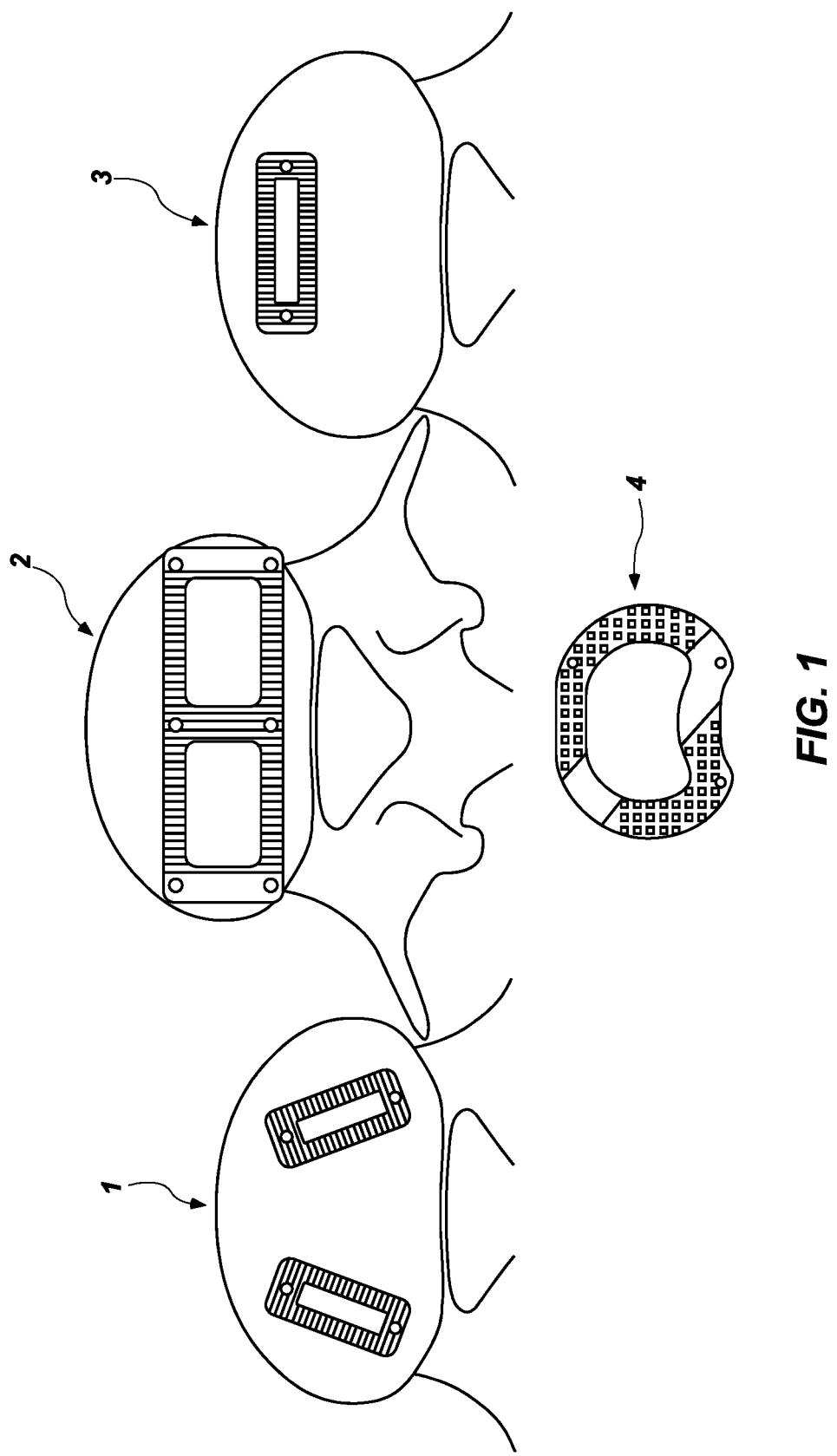
FIG. 1 is a front view of conventional intervertebral cages positioned on respective vertebral bodies.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

It must be noted that, as used in this specification and the appended claims, the singular forms "a," "an," and "the" include plural referents unless the context clearly dictates otherwise.

In describing and claiming the present disclosure, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

Applicant has discovered a novel apparatus and method for aligning, stabilizing and securing intervertebral cages adjacent spinal vertebrae as part of interbody fusion of the spine.

Applicant's method is an Anterior To Psoas (ATP) approach to the lumbar spine that passes anterior to the psoas muscle which overlies the lateral aspect of the spine. In an exemplary method, insertion of a lateral intervertebral cage is accomplished via movements at right angles with respect to the long axis of the spine. This exemplary method utilizes an anatomical channel, lateral annulus, to the spine anterior to the psoas which is accessed by a skin incision that leads to an oblique approach to the spine.

Applicant's method may be characterized by using a first retractor to expose a desired disc space in a spine and using a second retractor in cooperation with the first retractor to expose the desired disc space in the spine, wherein the second retractor includes a an L-shaped bracket and a curved arm, fixed to and extending from the L-shaped bracket. The curved arm includes a reverse tooth, or hook, extending from a terminal end of the curved arm. The curved arm and reverse tooth engage the psoas muscle and limits posterior retraction during an interbody fusion procedure. The curvature of the curved arm enables access to the lateral annulus while avoiding contact with bony anatomy, specifically the pelvis. After the desired disc space is exposed, an intervertebral cage can be sized and selected. Then an insertion tool, detailed below, may be used to insert and impact the selected intervertebral cage into a desired position. The insertion tool can then by disconnected from the cage and removed.

A curette or rake feature can then be attached to the insertion tool, or utilized as a completely separate independent tool, and inserted into the interior portion of the cage. The outer radius of the curette can substantially match the inner radius of the cage. The curette can then be used to scrape the surface of the endplate of the adjacent vertebra to prepare the surface for bone graft fusion. Because the curette radius substantially matches the interior radius of the cage, the entire desired surface can be scraped and prepared without any missed portions of the endplate surface or unnecessary scraping of portions of the endplate that will not come in contact with the bone graft.

When the endplate has been sufficiently prepared, bone graft material is then packed into the interior space of the cage and compressed, ensuring sufficient endplate contact for ideal fusion conditions. Then, a gate can be impacted and locked to the cage, thus securing the graft material in place and preventing graft extrusion, while also keeping the graft material under pressure against the endplate. The gate may also include spikes to resist unwanted movement and the gate may also include a keel or fin which can also help facilitate superior fixation and stability.

The aforementioned exemplary methods for interbody infusion reduce impaction forces on the front edge of the cage, thus reducing risk of cage fracture.

The Applicant's invention also includes an insertion tool which engages an intervertebral cage for insertion in a prepared disc space in a spine. In an exemplary embodiment, the insertion tool includes a handle, having a longitudinal axis, and an extended arm having at least two bends with respect to the axis of the handle. The two bends of the extended arm can enable a user to avoid bony anatomy, the pelvis for example, while accessing a desired disc space, and/or avoid soft tissue anatomy, such as when used in an ALIF procedure, for example. In another exemplary embodiment, each of the two bends may be equal to or greater than 90 degrees.

In an exemplary embodiment the extended arm may also include an attachment feature to secure a working attachment, such as, an intervertebral cage or curette to the insertion tool. In another exemplary embodiment the attachment feature may include a threaded shaft. The longitudinal axis of the treaded shaft may be coaxial with the longitudinal axis of the handle. The attachment feature may also include a mating plate, which substantially mimics the interior contours of a respective intervertebral cage, thereby providing additional support and stability to the cage during insertion.

In another exemplary embodiment the insertion tool may include two separate impaction points. A first impaction point may be located at a terminal end of the handle. A second impaction point may be located substantially at a bend in the extended arm of the insertion tool. In an exemplary embodiment a slap hammer attachment may be fixed to the terminal end of the handle to aid in removal of the insertion tool after insertion is completed. The extended arm may also include a twistable knob that is rotatably engaged with the attachment feature, facilitating threaded engagement between an intervertebral cage and the attachment feature.

The Applicant's invention can be characterized in an intervertebral cage having a frame coupled to a gate. In an exemplary embodiment, the gate may be hinged to the frame, enabling the gate to "open" with respect to the cage frame and enable a user to access the interior of the frame. In an exemplary embodiment the cage frame may be generally rectangular in shape having three sides with the gate acting as a fourth side. Alternatively the cage frame may include only two sides having a distal wall to support distal cortical rims with a posterior wall to prevent bone graft material from going too far posteriorly, and having no anterior wall.

The gate may also include a protrusion configured to mate with a locking feature on the frame, thereby locking the gate with respect to the frame, when the gate is fully engaged with the frame. In another exemplary embodiment, the gate may include a key portion that is configured to mate with a key-hole integral with the frame to enable aligned and secured engagement between the gate and the frame. In another exemplary embodiment, the key portion of the gate may include a protrusion that may be received by a locking feature on the frame, thereby locking the gate with respect to the frame when the two are fully engaged.

In an exemplary embodiment, the cage frame may include an attachment receiving feature, on an interior surface of the frame, configured to receive an attachment feature of an insertion tool. The gate may also include an attachment receiving feature, on an exterior surface of the gate, configured to receive an attachment feature of the insertion tool. In another exemplary embodiment, the attachment receiving features of the gate and frame may be threaded, to threadedly engage the attachment feature of an insertion tool.

In an exemplary embodiment, the frame may include substantially planar exterior surfaces. The planar exterior surface may include ridges that may extend over the entirety of the planar exterior surfaces and run in a substantially anterior-posterior direction. These ridges may aid in preventing back out of the cage after insertion, but enable vertebral translation during posterior correction.

In another exemplary embodiment, the intervertebral cage may include spikes, fins or shims fixed to an exterior surface of the frame and/or gate to improve gate and cage fixation during interbody fusion. A fin or plurality of fins may also be fixed to the top and bottom of the gate. The fins may be substantially straight or curved in a shape that matches the motion of the gate. The fin(s) can cut as the gate is closed and secured to the frame, thus providing additional fixation upon insertion.

Figure 2B:
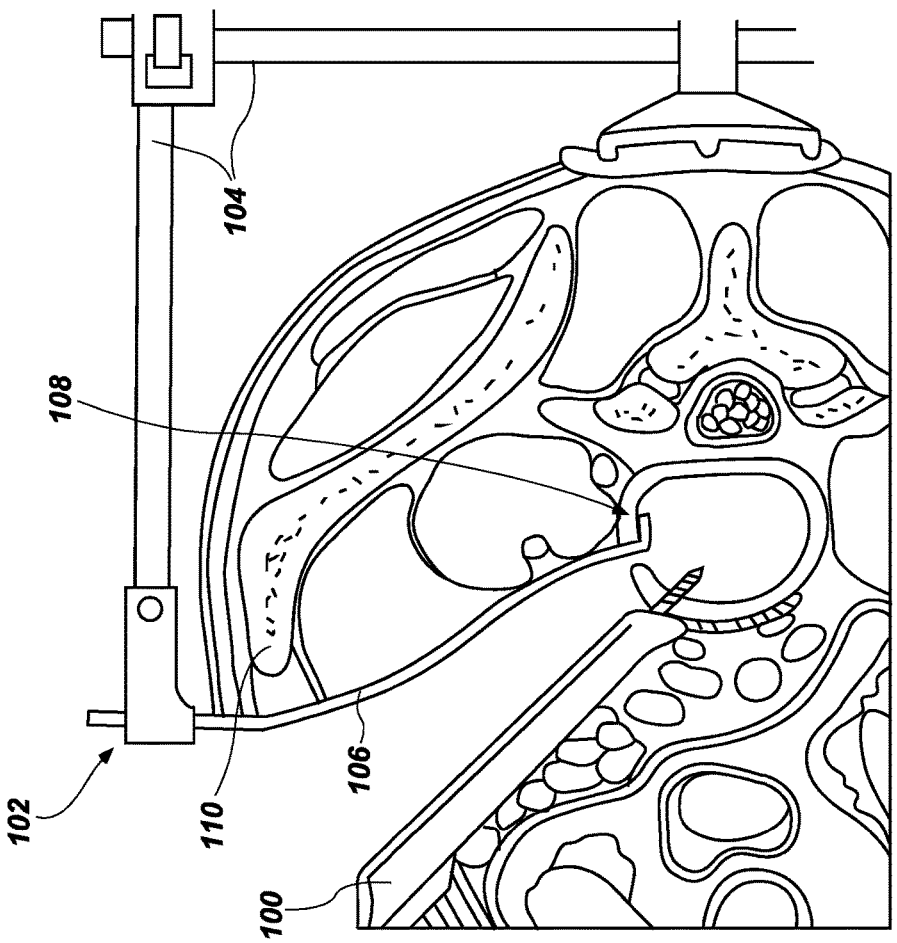
FIG. 2B is a cross-sectional side view an embodiment of the present disclosure.
Figure 2A:
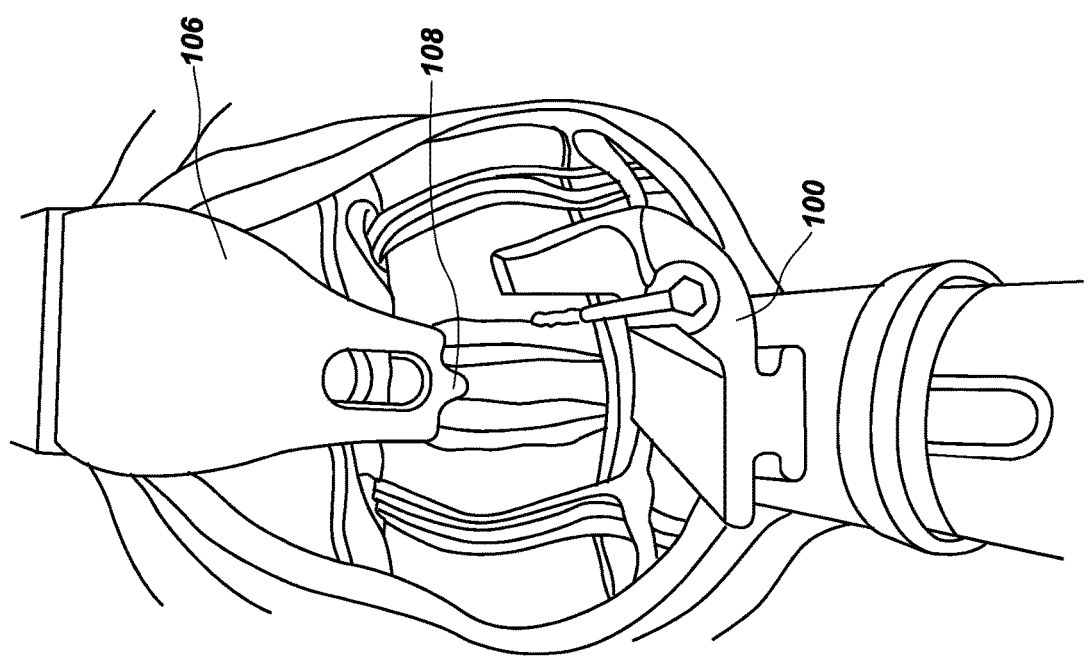
FIG. 2A is a top view of an embodiment of the present disclosure.

FIGS. 2A and 2B illustrate a top view and a cross-sectional side view of a first retractor 100 exposing a desired disc space in a spine. A second retractor 102 may be used in cooperation with the first retractor 100 to expose the desired disc space in the spine. The second retractor 102 includes a an L-shaped bracket 104 and a curved arm 106, fixed to and extending from the L-shaped bracket 104. The curved arm 106 includes a reverse tooth 108, or hook, extending from a terminal end of the curved arm 106. The curved arm 106 and reverse tooth 108 engage the psoas muscle and can limit posterior retraction during an interbody fusion procedure. For example, the reverse tooth 108 can be inserted inside the disc space underneath and uncut portion of an annulus of a disc. An opening into the disc space can be formed by a cut made in an outer part of the disc, which is the annulus. The cut in the annulus can act as a window through which the disc space is accessed for, but not limited to, removal of a nucleus, endplate preparation and/or insertion of cage, for example. An outer surface of the opening may be an tough, outer, uncut annulus of the disc. This tough outer annulus can be engaged by a portion of the curved arm 106 adjacent to the reverse tooth 108, which can be used to limit the posterior retraction of curved arm 106, thus limiting and controlling retraction of psoas by the curved arm 106, which may also avoid excessive retraction of the psoas with resultant compression of nerves traveling within psoas. The reverse tooth 108 can keep the curved arm 106 from lifting up out of the annulus, which the portion of the curved arm 106 adjacent to the reverse tooth 108 can limit posterior retraction. Thus, the curvature of the curved arm 106 may enable access to the lateral annulus while avoiding contact with bony anatomy, specifically the pelvis 110, and/or soft tissue anatomy, such as when used in an ALIF procedure, for example.

FIGS. 3A and 3B illustrate a top view and a cross-sectional side view of the first and second retractors 100 and 102, respectively, and also illustrates, an insertion tool 111. The insertion tool 111 can engage a cobb 112 or curette to prepare a disc space for insertion of a cage. The insertion tool 111 includes a handle 114, having a longitudinal axis, and an extended arm 116 having a first bend and a second bend 120 with respect to the axis of the handle 114. The two bends 118 and 120 of the extended arm 116 can enable a user to avoid the pelvis 110 while accessing a desired disc space. Each of the two bends 118 and 120 may be equal to or greater than 90 degrees.

The curette feature 112 can then be removably attached to the insertion tool 111, or utilized as a completely separate independent tool. The outer radius of the curette 112 substantially matches the inner radius of the intervertebral cage that with be inserted during the interbody infusion procedure. The curette 112 can be used to scrape the surface of the endplate of the adjacent vertebra to prepare the surface for bone graft fusion.

Figures 4A, 4B:
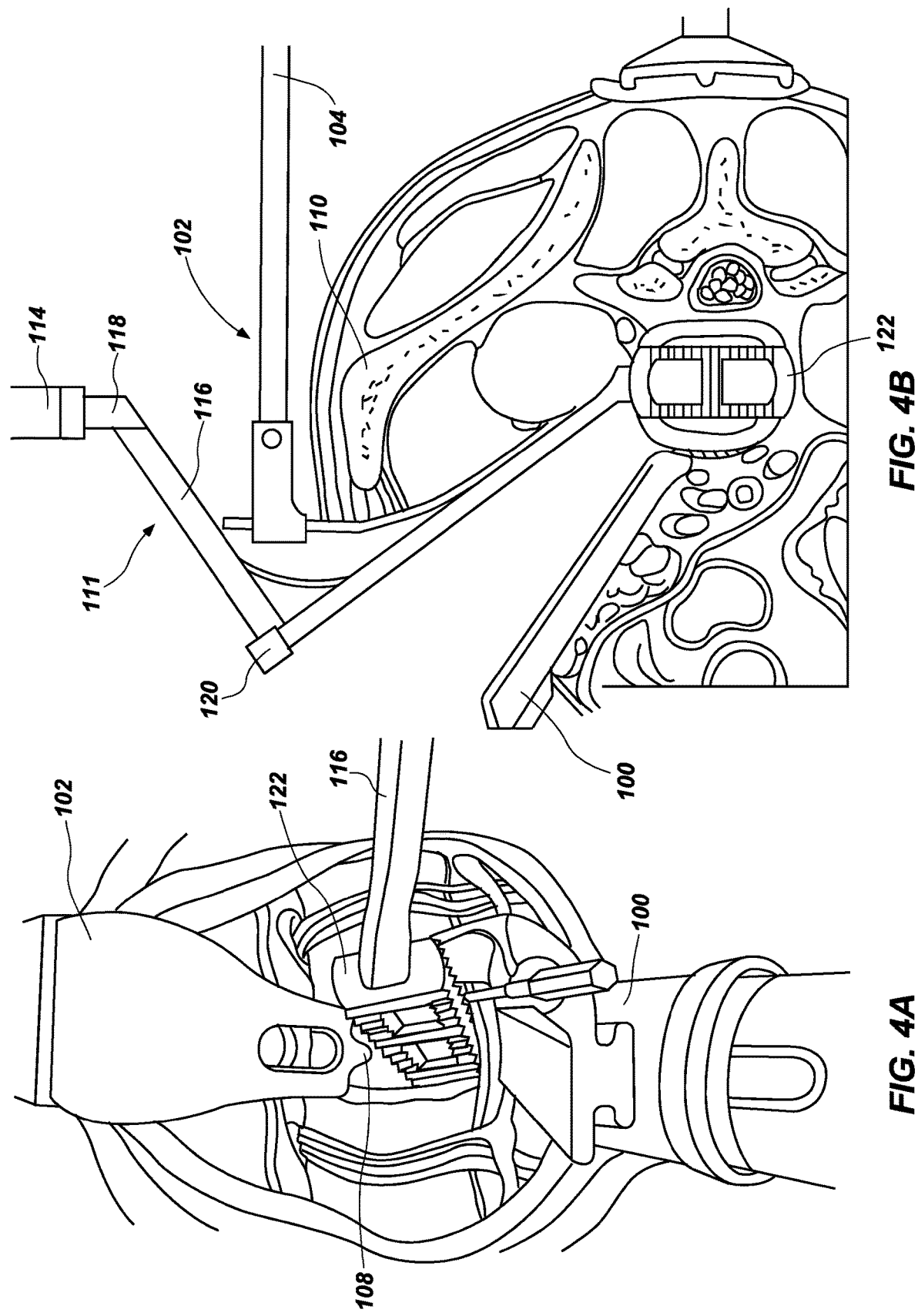
FIG. 4A is a top view and cross-sectional side view of another embodiment of the present disclosure.
FIG. 4B is a cross-sectional side view of another embodiment of the present disclosure.

FIGS. 4A and 4B illustrate a top view and a cross-sectional side view of the first and second retractors 100 and 102, respectively, and also illustrates, the insertion tool 111. The insertion tool 111 can engage a conventional intervertebral cage 122 for insertion.

Figure 5:
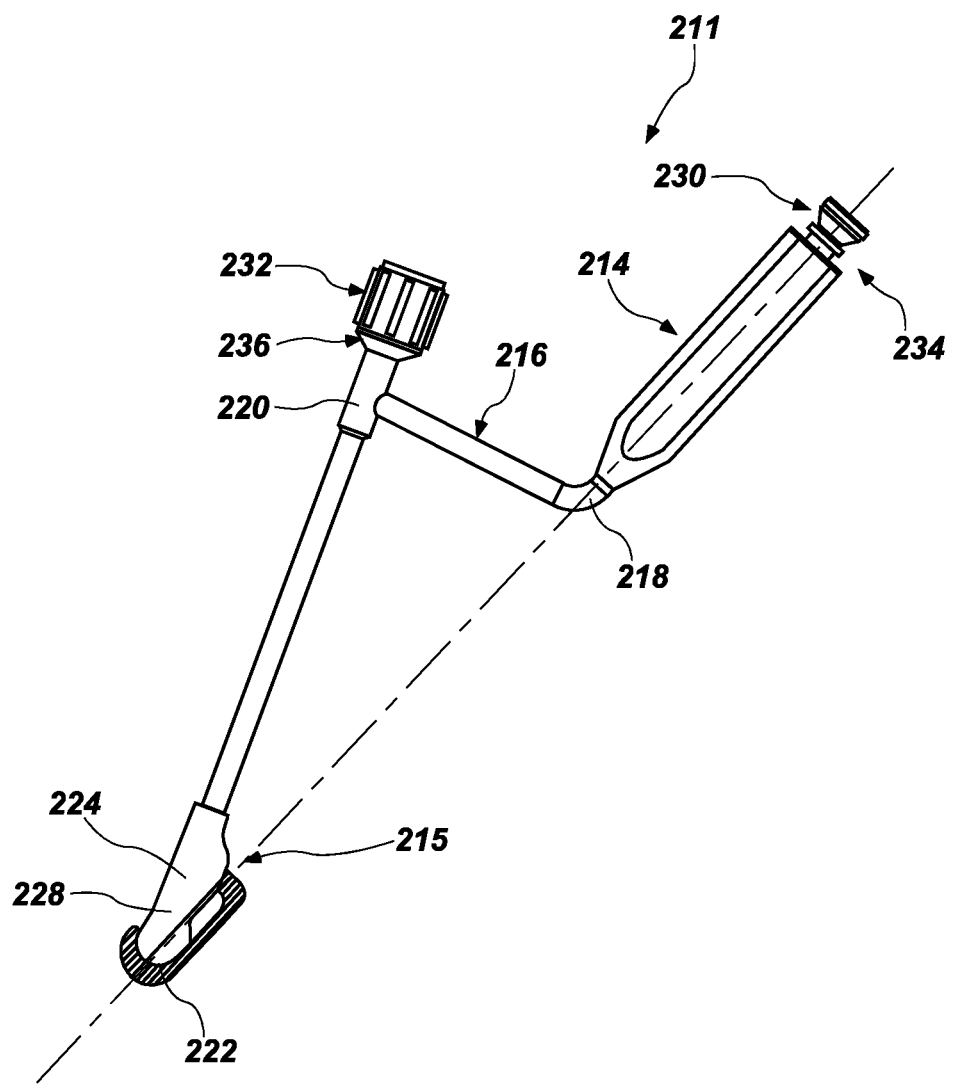
FIG. 5 is a side view of an insertion tool embodiment of the present disclosure.

FIG. 5 illustrates a side view of an exemplary embodiment of an insertion tool 211 which engages an exemplary embodiment of an intervertebral cage 222 for insertion in a prepared disc space in a spine. The insertion tool 211 includes a handle 214, having a longitudinal axis 215, and an extended arm, designated generally at 216, having at a first bend 218 and a second bend 220 with respect to the axis 215 of the handle 214. The concept of a "bend" in arm 216 shall be construed broadly to mean a change in direction of the arm whether arm is unitary or a combination of joined arm segments. The two bends 218 and 220 may, each form or include an angle that is equal to or greater than 90 degrees. The two bends 218 and 220 may instead, if desired, each form or include an angle that is equal to or less than 90 degrees The extended arm 216 may also include an attachment feature 224 to secure the intervertebral cage 222 to the insertion tool 211, such that a longitudinal axis of the intervertebral cage 222 may be coaxial, or substantially coaxial, with the longitudinal axis 215 of the handle 214. FIG. 5 illustrates that longitudinal axis 215 may represent the longitudinal axis of both the handle 214 and the intervertebral cage 222, which are coaxial, or substantially coaxial. As used herein, the phrase "substantially coaxial" includes, but is not limited to, a straight line that passes through a distal end of the handle 214 and a proximal end of the handle 214, with the same straight line passing through a distal end of the intervertebral cage 222 and a proximal end of the intervertebral cage 222. It is to be understood that the existence of any straight line which satisfies the foregoing, whether that straight line is imaginary or actual, shall also mean the existence of a handle (such as handle 214) and an intervertebral cage (such as intervertebral cage 222) that are coaxial or substantially coaxial. It is further to be understood that the concept of a distal end or a proximal end of an object, such as handle 214 or intervertebral cage 222, may exist as part of the object regardless of whether the distal or proximal end constitutes a terminal end. Additionally, the longitudinal axis of the intervertebral cage 222 may be substantially parallel with, but spaced apart from, the longitudinal axis of the handle 214.

Figure 6:
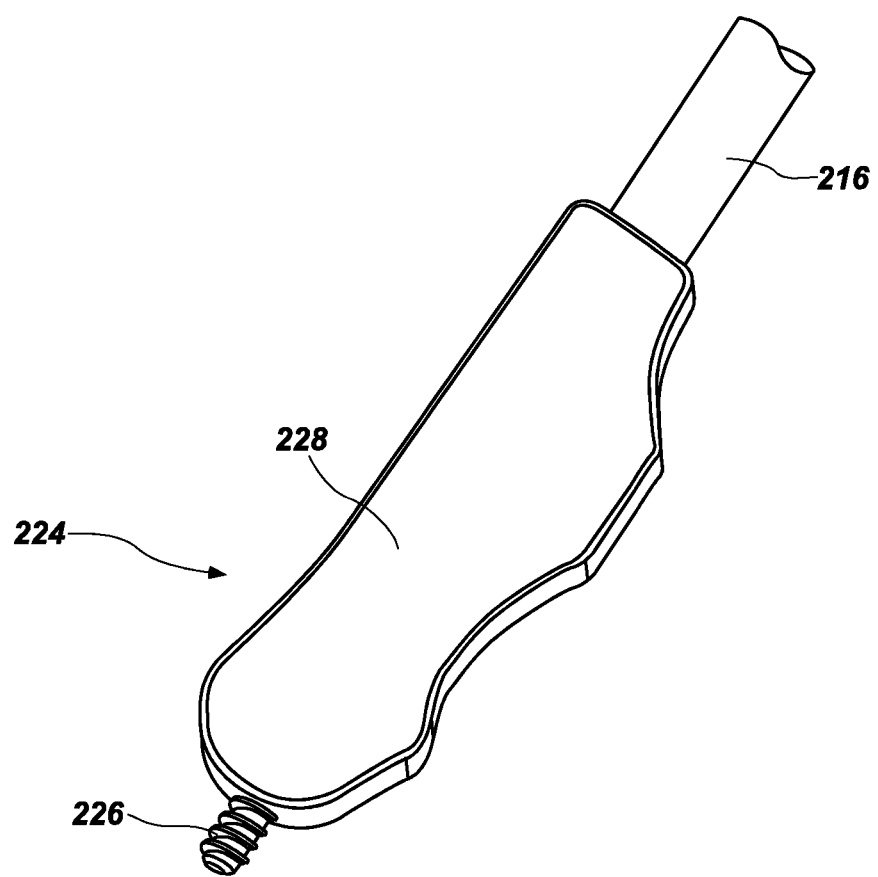
FIG. 6 is an enlarged side view of the insertion tool of FIG. 5.

FIG. 6 is an enlarged side view of the attachment feature 224 having a threaded shaft 226. The longitudinal axis of the threaded shaft 226 is coaxial, or substantially coaxial, with the longitudinal axis 215 of the handle 214, and is also represented by longitudinal axis 215, as shown in FIG. 5. As used herein, the phrase "substantially coaxial" includes, but is not limited to, a straight line that passes through the distal end of the handle 214 and the proximal end of the handle 214, with the same straight line passing through a distal end of the threaded shaft 226 and a proximal end of the threaded shaft 226.

The attachment feature 224 may also include a mating plate 228, which substantially mimics the interior contours of the intervertebral cage 222, thereby providing additional support and stability to the cage 222 during insertion.

The insertion tool 211 also includes a first impaction point 230 and a second impaction point 232. The first impaction point 230 is located at a terminal end of the handle 214. The second impaction point 232 may be located substantially at the second bend 220 in the extended arm 216. A slap hammer attachment 234 is fixed to the terminal end of the handle 214 to aid in removal of the insertion tool 211 after insertion is completed. The extended arm 216 may also include a twistable knob 236 that is rotatably engaged with the attachment feature 224, specifically the threaded shaft 226 facilitating threaded engagement between the intervertebral cage 222 and the threaded shaft 226.

FIGS. 7A and 7B illustrate perspective views of an exemplary embodiment of an intervertebral cage 300 having a frame 302 uncouple from a gate 304 and a second view with the gate 304 coupled to the frame 302. The cage frame includes a distal wall 305 to support distal cortical rims and a posterior wall 306 to prevent bone graft material from going too far posteriorly. The gate 304 includes a key portion 308 configured to mate with a key-hole 310 integral with the frame 302 to enable aligned and secured engagement between the gate 304 and the frame 302.

The frame 302 also includes an attachment receiving feature 320, on an interior surface, configured to receive an attachment feature of an insertion tool. The gate 304 may also include an attachment receiving feature 322, on an exterior surface, configured to receive an attachment feature of an insertion tool. The attachment receiving features 320 and 322 of the gate 304 and frame 302 may be threaded, to threadedly engage the attachment feature of an insertion tool.

Figure 8:
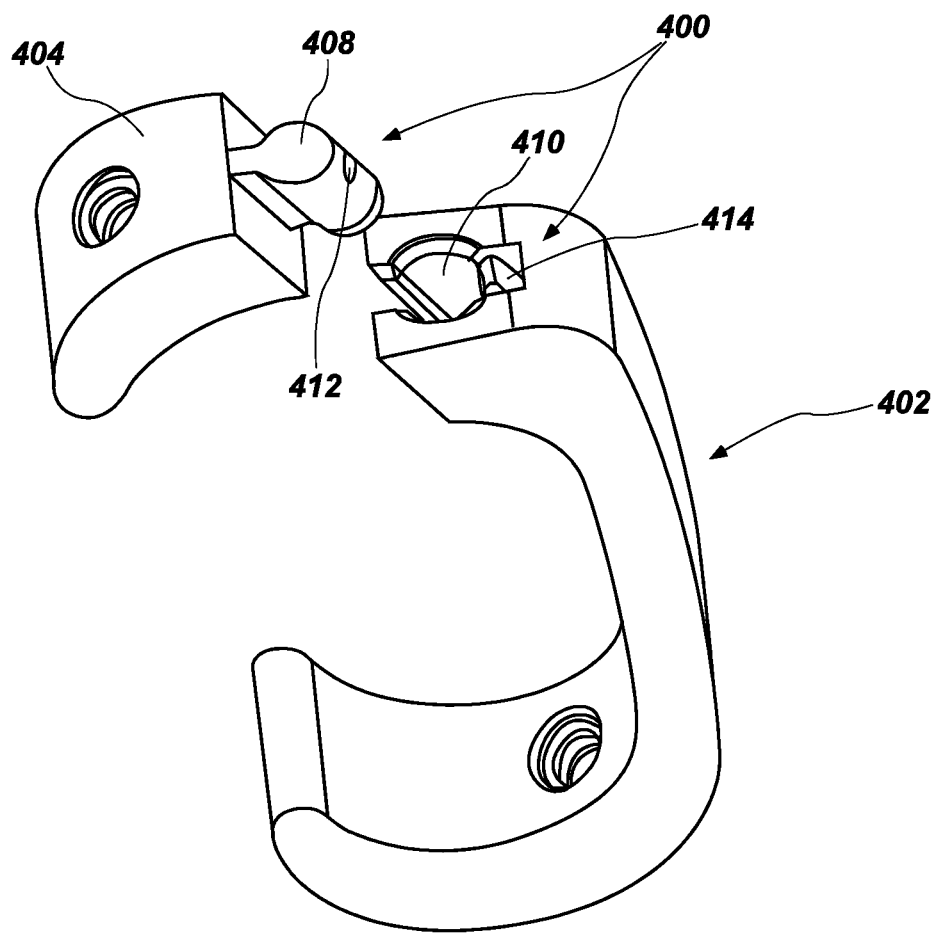
FIG. 8 is a perspective view of another intervertebral cage of the present disclosure.

FIG. 8 illustrates a perspective view of another exemplary embodiment of an intervertebral cage 400. Cage 400 includes a frame 400 and a gate 404. The gate 404 includes a key portion 408 configured to mate with a key-hole 410 integral with the frame 402. The key portion 408 of the gate 404 may include a protrusion 412 that may be received by a locking feature 414 on the frame 402, thereby locking the gate 404 with respect to the frame 402 when the two are fully engaged.

Figure 9B:
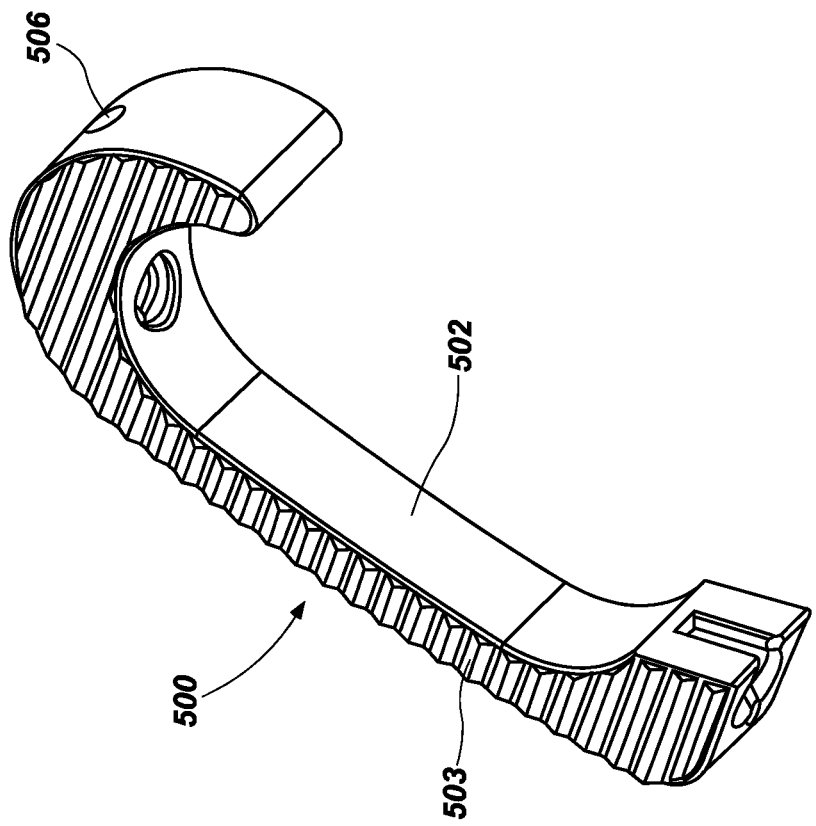
FIG. 9B is a top view of another intervertebral cage of the present disclosure.
Figure 9A:
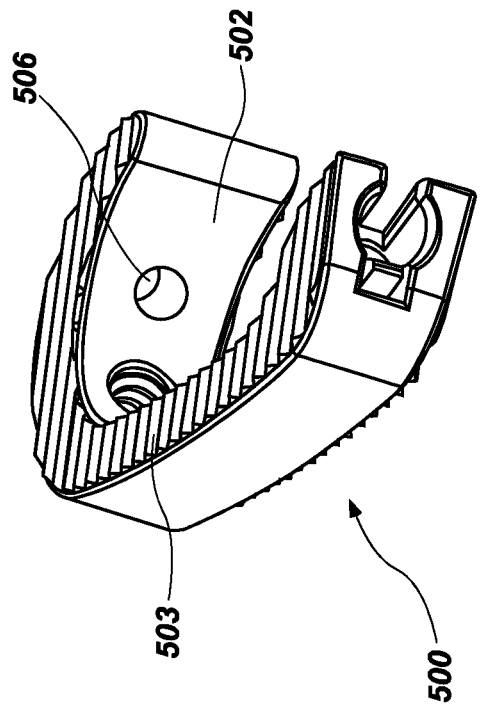
FIG. 9A is a perspective view of another intervertebral cage of the present disclosure.

FIGS. 9A and 9B illustrate perspective views of an exemplary embodiment of an intervertebral cage 500. Cage 500 includes a frame 502 configured to mate with a gate (the gate is not shown). The frame 502 includes substantially planar exterior surfaces. The planar exterior surfaces include ridges 503 that extend over the entirety of the planar exterior surfaces and run in a substantially anterior-posterior direction. These ridges 503 aid in preventing back out of the cage 500 after insertion, but enable vertebral translation during posterior correction. The frame also includes a through hole 506 that can be used to facilitate contralateral removal of cage 500.

Figure 10B:
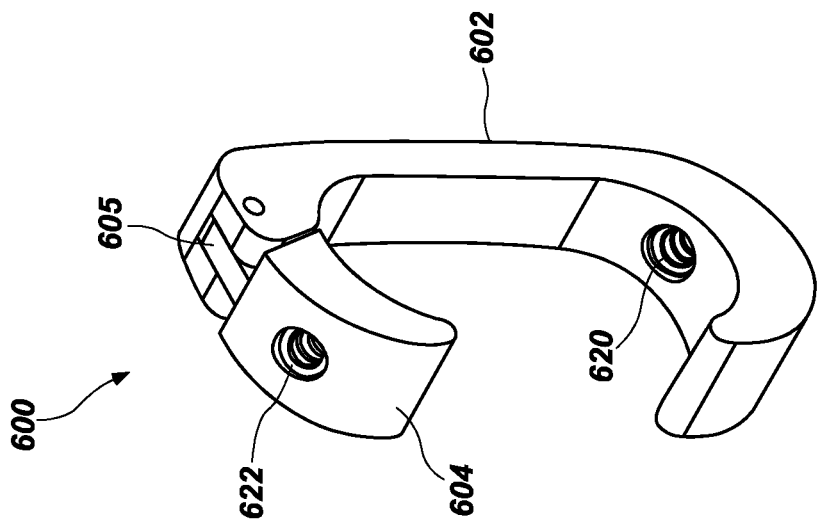
FIG. 10B is a perspective view of another intervertebral cage of the present disclosure.
Figure 10A:
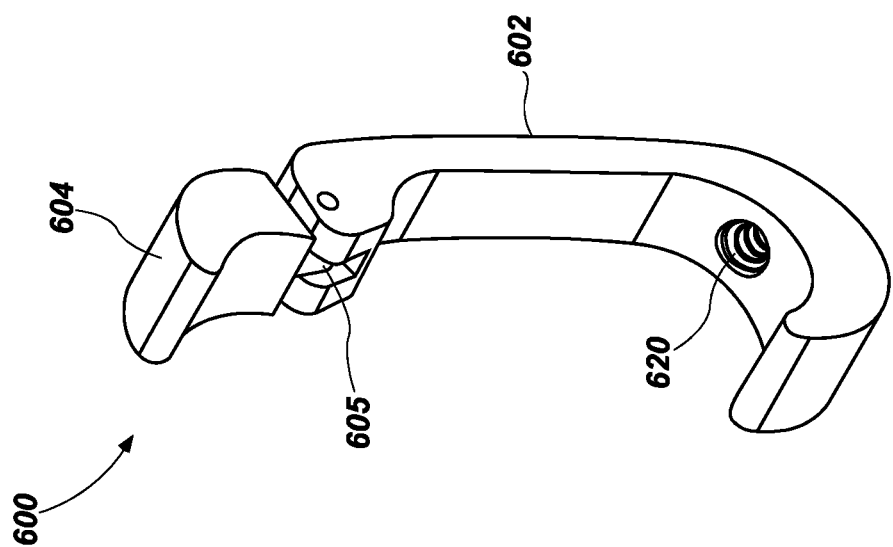
FIG. 10A is a perspective view of an open intervertebral cage of the present disclosure.

FIGS. 10A and 10B illustrate perspective views of an exemplary embodiment of an intervertebral cage 600 having a frame 602 hinged to a gate 604. In the first view the gate 604 is "open" with respect to the frame 602 and the second view shows the gate 604 in a "closed" position. A hinge 605 pivotally couples the frame 602 to the gate 604, enabling a user to access the interior of the cage 600 for insertion and packing grafting material. The hinge 605 then enables a user to close the gate 604, thereby securing the grafting material within the cage 600.

The frame 604 also includes an attachment receiving feature 620, on an interior surface, configured to receive an attachment feature of an insertion tool. The gate 604 also includes an attachment receiving feature 622, on an exterior surface, configured to receive an attachment feature of an insertion tool. The attachment receiving features 620 and 622 of the gate 604 and frame 602 may be threaded, to threadedly engage the attachment feature of an insertion tool.

FIGS. 11A and 11B illustrate perspective views of an exemplary embodiment of an intervertebral cage 700 having a frame 702 hinged to a gate 704. The shape of cage 700 conforms most closely to a anterior lumbar interbody fusion (ALIF) style cage. In the first view the gate 704 is "closed" with respect to the frame 702 and the second view shows the gate 704 in an "open" position. A hinge 705 pivotally couples the frame 702 to the gate 704, enabling a user to access the interior of the cage 700 for insertion and packing grafting material. The hinge 705 then enables a user to close the gate 704, thereby securing the grafting material within the cage 700.

The frame 704 also includes an attachment receiving feature 720, on an interior surface, configured to receive an attachment feature of an insertion tool. The gate 704 also includes an attachment receiving feature 722, on an exterior surface, configured to receive an attachment feature of an insertion tool. Attachment receiving feature 720 of the frame 702 may be threaded, to threadedly engage the attachment feature of an insertion tool.

The gate 704 may also include a protrusion 712 configured to mate with a locking feature 714 on the frame 702, thereby locking the gate 704 with respect to the frame 702, when the gate 704 is fully engaged with the frame 702.

The frame 702 also includes substantially planar exterior surfaces. The planar exterior surfaces include ridges 703 that extend over the entirety of the planar exterior surfaces and run in a substantially anterior-posterior direction. These ridges 703 aid in preventing back out of the cage 700 after insertion, but enable vertebral translation during posterior correction.

Figure 12:
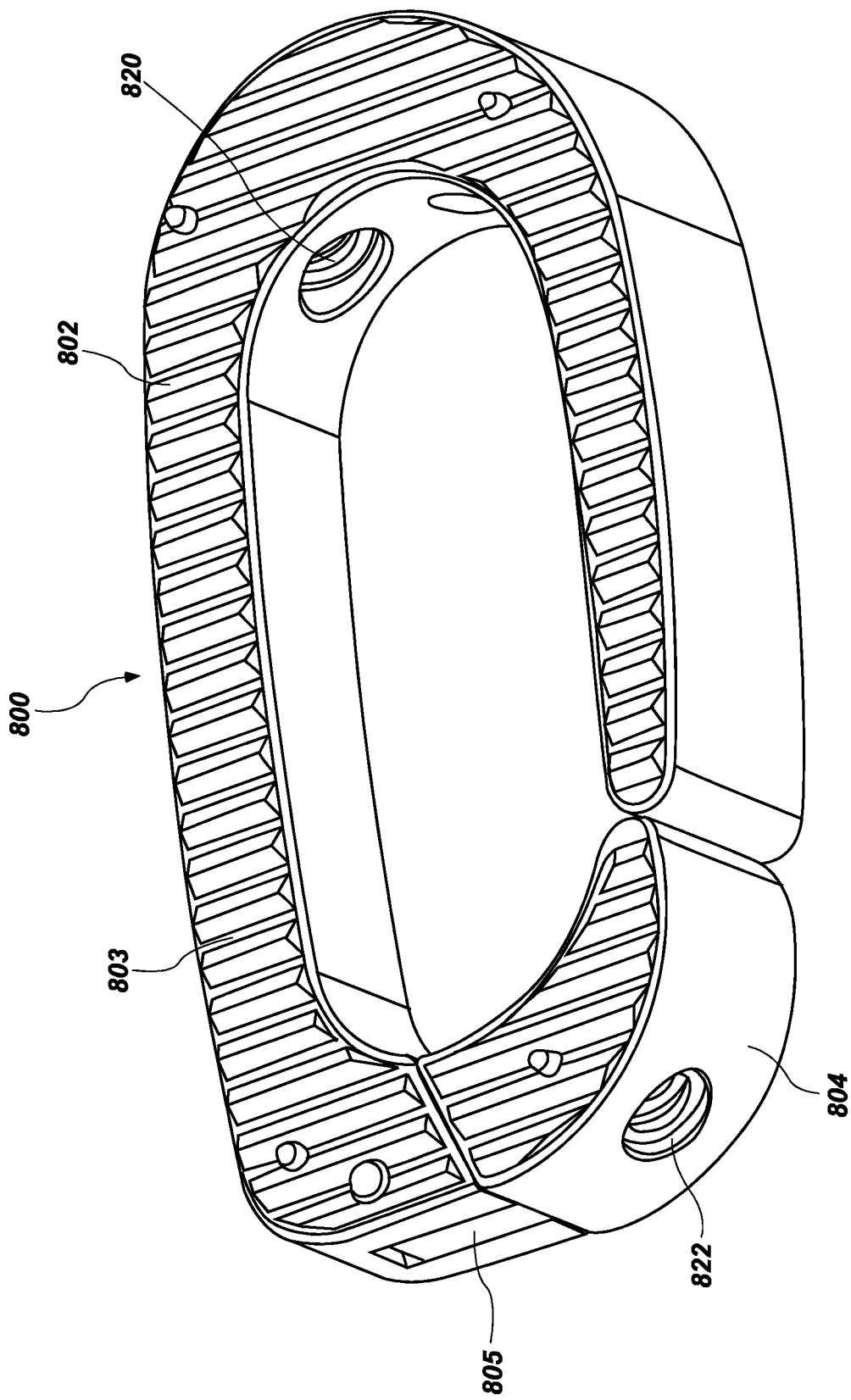
FIG. 12 is a perspective view of another intervertebral cage of the present disclosure.

FIG. 12 illustrates a perspective view of an exemplary embodiment of an intervertebral cage 800 having a frame 802 hinged to a gate 804. The shape of cage 800 conforms most closely to a lateral lumbar interbody fusion (LLIF) style cage. In FIG. 12, gate 804 is "closed" with respect to the frame 802. A hinge 805 pivotally couples the frame 802 to the gate 804, enabling a user to access the interior of the cage 800 for insertion and packing grafting material. The hinge 805 then enables a user to close the gate 804, thereby securing the grafting material within the cage 800.

The frame 804 also includes an attachment receiving feature 820, on an interior surface, configured to receive an attachment feature of an insertion tool. The gate 804 also includes an attachment receiving feature 822, on an exterior surface, configured to receive an attachment feature of an insertion tool. Attachment receiving features 820 and 822 are threaded, to threadedly engage the attachment feature of an insertion tool.

The frame 802 also includes substantially planar exterior surfaces. The planar exterior surfaces include ridges 803 that extend over the entirety of the planar exterior surfaces and run in a substantially anterior-posterior direction. These ridges 803 aid in preventing back out of the cage 800 after insertion, but enable vertebral translation during posterior correction.

In another exemplary embodiment, an intervertebral cage may include spikes, fins or shims fixed to an exterior surface of the frame and/or gate to improve gate and cage fixation during interbody fusion. A fin or plurality of fins may also be fixed to the top and bottom of the gate. The fins may be substantially straight or curved in a shape that matches the motion of the gate. The fin(s) can cut as the gate is closed and secured to the frame, thus providing additional fixation upon insertion.

In accordance with the features and combinations described above, an intervertebral cage for infusing bone graft material to an endplate of a vertebra may comprise:

a frame having a plurality of sides defining an interior opening;

a gate coupled to at least one of the sides of the frame, wherein the coupling between the frame and the gate is a hinge.

An interior surface of the frame of the intervertebral cage can be coupled an insertion tool.

An exterior surface of the gate of the intervertebral cage can be coupled an insertion tool.

The gate includes an protrusion that is secured within a locking feature fixed to the frame when the gate is in a closed position with respect to the frame.

The gate also includes at least one of the following fixation aides: screw holes, spikes or fins.

In accordance with the features and combinations described above, an intervertebral cage for infusing bone graft material to an endplate of a vertebra may comprise:

a frame having a plurality of sides defining an interior opening;

a gate coupled to at least one of the sides of the frame, wherein the coupling between the frame and the gate is key and lock engagement feature.

The gate includes a key feature that mates with a key-hole feature of frame.

In accordance with the features and combinations described above, an intervertebral cage insertion tool may comprise:

a handle having a longitudinal axis;

a extended arm fixed to the handle and having at least two bends to avoid bony features during insertion of an intervertebral cage;

an attachment feature configured to attach an intervertebral cage to the insertion tool such that the longitudinal axis of the intervertebral cage is substantially coaxial with the handle.

The attachment feature includes a mating plate that is shaped to substantially match the contour of an interior surface of the intervertebral cage.

In accordance with the features and combinations described above, a useful method of intervertebral cage insertion includes the steps of:

preparing a disc space in the spine for insertion of an intervertebral cage;

attaching an intervertebral cage frame to an insertion tool, wherein the insertion tool includes a handle and an arm extending from the handle, the arm having at least two bends, to avoid bony features during insertion;

impacting the intervertebral cage frame into the disc space using the insertion tool;

removing the insertion tool from the intervertebral cage frame;

packing the intervertebral cage frame with bone grafting material;

impacting a gate coupled to the intervertebral cage frame, securing the bone grafting material within the intervertebral cage, wherein the gate is couple to the cage frame via a hinge.

In accordance with the features and combinations described above, an intervertebral cage insertion tool may comprise:

a handle having a longitudinal axis;

an extended arm fixed to the handle and having at least two bends to avoid bony features during insertion of an intervertebral cage;

an attachment feature configured to attach an intervertebral cage to the insertion tool such that the longitudinal axis of the intervertebral cage is substantially coaxial with the handle, wherein the attachment feature includes a mating plate that is shaped to substantially match a contour of an interior surface of the intervertebral cage;

an exterior surface of the gate of the intervertebral cage having an attachment receiving feature configured to be coupled an insertion tool, wherein the gate includes a protrusion that is secured within a locking feature fixed to the frame when the gate is in a closed position with respect to the frame, and wherein the gate includes a key feature that mates with a key-hole feature of frame; and wherein an interior surface of the frame of the intervertebral cage includes an attachment receiving feature configured to be coupled an insertion tool.

In accordance with the features and combinations described above, an intervertebral cage for infusing bone graft material to an endplate of a vertebra, may comprise:

a frame having a plurality of sides defining an interior opening; and a gate coupled to at least one of the sides of the frame, wherein the coupling between the frame and the gate is a hinge;

an exterior surface of the gate of the intervertebral cage having an attachment receiving feature configured to be coupled an insertion tool;

wherein an interior surface of the frame of the intervertebral cage includes an attachment receiving feature configured to be coupled an insertion tool.

wherein the intervertebral cage is configured to engage the insertion tool, the insertion tool having an attachment feature including a mating plate that is shaped to substantially match a contour of an interior surface of the intervertebral cage.

In accordance with the features and combinations described above, a useful method of intervertebral cage insertion includes the steps of:

preparing a disc space in a spine for insertion of an intervertebral cage;

attaching an intervertebral cage frame to an insertion tool, wherein the insertion tool includes a handle and configured to avoid bony features during insertion of the intervertebral cage frame, the insertion tool including an attachment feature having a mating plate that is shaped to substantially match a contour of an interior surface of the intervertebral cage;

inserting the intervertebral cage frame utilizing a lateral annulus, anterior to a psoas muscle, via an oblique approach the spine;

impacting the intervertebral cage frame into the disc space using the insertion tool;

removing the insertion tool from the intervertebral cage frame;

packing the intervertebral cage frame with bone grafting material after the intervertebral cage frame has been impacted into the disc space; and impacting a gate coupled to the intervertebral cage frame, securing the bone grafting material within the intervertebral cage, wherein the gate is couple to the cage frame via a hinge.

It is to be understood that the above-described arrangements are only illustrative of the application of the principles of the present disclosure. Numerous modifications and alternative arrangements may be devised by those skilled in the art without departing from the spirit and scope of the present disclosure are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

The invention claimed is:

1. An intervertebral cage insertion tool assembly comprising:
a handle having a longitudinal axis;
an intervertebral cage attached to the insertion tool such that a longitudinal axis of the intervertebral cage is substantially coaxial with the longitudinal axis of the handle;
an extended arm fixed to the handle and having a first segment extending away from the longitudinal axis of the handle, and a second segment connected to the first segment, wherein the second segment extends towards the longitudinal axis of the handle, to avoid bony features during insertion of the intervertebral cage, and wherein the extended arm terminates at an attachment feature, and wherein the extended arm has a first bend that intersects the longitudinal axis of the handle and a second bend that joins the first segment and the second segment of the extended arm;
the attachment feature configured to attach the intervertebral cage to the insertion tool such that the longitudinal axis of the intervertebral cage is substantially coaxial with the handle and a portion of the attachment feature intersects the longitudinal axis of the handle.

2. The intervertebral cage insertion tool assembly of claim 1, wherein the attachment feature includes a mating plate that is shaped to substantially match a contour of an interior surface of the intervertebral cage.

3. The intervertebral cage insertion tool assembly of claim 1, wherein
the intervertebral cage includes a gate, and an exterior surface of the gate of the intervertebral cage having an attachment receiving feature configured to be coupled to the insertion tool.

4. The intervertebral cage insertion tool assembly of claim 1, wherein the intervertebral cage includes a frame and a gate, and the gate includes a protrusion that is secured within a locking feature fixed to the frame when the gate is in a closed position with respect to the frame.

5. The intervertebral cage insertion tool assembly of claim 1, wherein the intervertebral cage includes a frame and a gate, and wherein the gate includes a key that mates with a key-hole of the frame.

6. The intervertebral cage insertion tool assembly of claim 1, wherein the intervertebral cage includes a frame, and an interior surface of the frame of the intervertebral cage includes an attachment receiving feature configured to be coupled the insertion tool.

7. The intervertebral cage insertion tool assembly claim 1, wherein the intervertebral cage includes a frame and a gate, and wherein the gate includes a key that mates with a key-hole of the frame.

8. The intervertebral cage insertion tool assembly of claim 1, wherein the longitudinal axis of the intervertebral cage is substantially parallel with, but spaced apart from, the longitudinal axis of the handle.

9. An intervertebral cage insertion tool assembly comprising:
a handle having a longitudinal axis;
an intervertebral cage attached to the insertion tool such that a longitudinal axis of the intervertebral cage is substantially coaxial with the longitudinal axis of the handle;
an extended arm having a first portion fixed to the handle, the first portion extending away from the longitudinal axis of the handle, and the extended arm having a second portion connected to the first portion, wherein the second portion extends towards the longitudinal axis of the handle, to avoid bony features during insertion of the intervertebral cage, and wherein the extended arm terminates at an attachment feature, and wherein the extended arm has a first bend that intersects the longitudinal axis of the handle and a second bend that joins the first portion and the second portion of the extended arm;
the attachment feature configured to attach the intervertebral cage to the insertion tool such that the longitudinal axis of the handle intersects a portion of the intervertebral cage.

10. The intervertebral cage insertion tool assembly of claim 9, wherein the longitudinal axis of the intervertebral cage is substantially parallel with, but spaced apart from, the longitudinal axis of the handle.

\* \* \* \* \*